United States Patent [19]

Kalopissis et al.

[11] 4,008,272
[45] Feb. 15, 1977

[54] N-THIOUREIDO AND N-UREIDO PHENYLENE DIAMINES AND METHOD OF PREPARING SAME

[75] Inventors: Gregoire Kalopissis; Jean Gascon, both of Paris; Andree Bugaut, Boulogne sur Seine; Jacqueline Gallien, La Garenne-Colombes; Hubert Gaston-Breton, Paris, all of France

[73] Assignee: Societe Anonyme dite: L'Oreal, Paris, France

[22] Filed: May 16, 1975

[21] Appl. No.: 578,318

Related U.S. Application Data

[60] Continuation of Ser. No. 247,892, April 26, 1972, abandoned, which is a division of Ser. No. 854,784, Sept. 2, 1969, Pat. No. 3,697,215.

[30] Foreign Application Priority Data

Sept. 9, 1968 Luxembourg .......................... 56846
Jan. 16, 1969 Luxembourg .......................... 57792

[52] U.S. Cl. .......................... 260/552 R; 260/553 A
[51] Int. Cl.[2] ................. C07C 85/102; C07C 87/52
[58] Field of Search ....... 260/553 A, 552 R, 553 R; 8/11

[56] References Cited

UNITED STATES PATENTS

| | | | |
|---|---|---|---|
| 1,932,901 | 10/1933 | Lehmann et al. ........................ | 8/11 |
| 3,134,721 | 5/1964 | Seemuller et al. .................... | 8/11 X |
| 3,231,471 | 1/1966 | Lange .................................. | 8/11 X |
| 3,634,478 | 1/1972 | Halasz et al. .................. | 260/553 A |

*Primary Examiner*—Allen B. Curtis
*Attorney, Agent, or Firm*—Cushman, Darby & Cushman

[57] ABSTRACT

Dye compositions containing the oxidation dye:

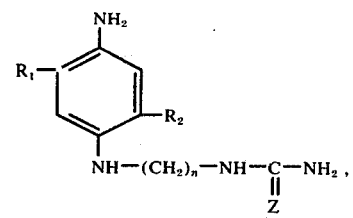

and the method of using it to dye live human hair.

12 Claims, No Drawings

N-THIOUREIDO AND N-UREIDO PHENYLENE DIAMINES AND METHOD OF PREPARING SAME

This is a continuation of application Ser. No 247,892, now abandoned, filed Apr. 26, 1972, which in turn, is a division of Ser. No. 854,784, filed Sept. 2, 1969, now U.S. Pat. No. 3,697,215.

SUMMARY OF THE INVENTION

Certain known methods of dyeing keratinic fibers, and in particular human hair, utilize dyeing compositions comprising oxidation dyes, and in particular aromatic ortho or para-diamines which are generally referred to as "oxidation bases". The shades obtained with these bases may be varied by using color modifiers or "couplers" and, in particular, aromatic metadiamines or meta-aminophenols.

It is the object of the present invention to provide a new class of bases which may be utilized in dyeing keratinic fibers.

It is a further object of the present invention to provide as a new article of manufacture a composition for dyeing keratinic fibers, and in particular human hair, which is characterized by the fact that it comprises, possibly in association with one or more couplers, at least one base responding to the following general formula:

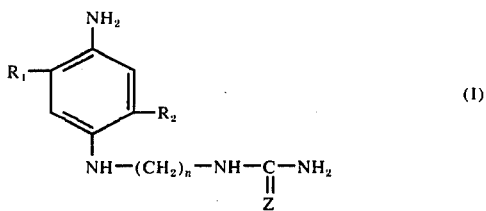

in which $R_1$ and $R_2$ may be the same or different and represent hydrogen, halogen, alkoxy having 1–3 carbon atoms and alkyl having 1–3 carbon atoms, and preferably methyl or methoxy, Z represents oxygen or sulfur, and $n$ is a whole number between 2 and 4 inclusive.

The compounds according to formula I may of course be used in the form of their acid addition salts.

Among the couplers which may be advantageously used with the bases of formula I are: meta-aminophenol, 3-N-carbamylmethylamino-phenol, resorcinol, meta-phenylene diamine, 2,4-diamino-anisole sulfate, 3-hydroxy-phenylurea.

When couplers are used in association with the bases of formula I, the ratio of base to coupler may vary within broad limits, but an excess of coupler is preferably used. The preferred base to coupler ratio is from 1:1 to 1:4.

In the dyeing compositions of the invention the concentration of the formula I base is between 0.1 and 10% by weight.

The dyeing compositions of the invention may also contain other dyes useful under the same conditions, such as direct dyes (e.g. azo or anthraquinone dyes). They may also contain bases other than those defined above, in association with couplers.

The dyeing composition of the invention may also contain wetting agents, dispersing agents, penetrating agents, and any other ingredients conventionally used in the dyeing of human hair. They may take the form of an aqueous solution, a cream or a gel, or may contain a liquified gas permitting them to be vaporized and packaged in aerosol containers.

The dyeing compositions of the invention are utilized in a conventional manner at an alkaline pH, preferably between 8 to 10. This pH may be obtained by adding a base such as for example ammonia. The product is applied to the hair in the presence of an oxidizing solution, which is preferably hydrogen peroxide.

One of the essential advantages of the dyeing compositions of the invention is that it gives tints which are highly resistant to discoloration by light, inclement weather, and washing.

It is a further object of the present invention to provide a process for dyeing hair which is characterized by the fact that, after adding hydrogen peroxide to a dyeing composition as above defined, and rendering said composition alkaline by adding a base such as for example ammonia it is applied to the hair, which is then rinsed, shampooed and dried.

A further object of the present invention is to provide as a new article of manufacutre the compounds of formula I.

The N-($\omega$-ureidoalkyl) paraphenylene diamines, that is to say those compounds of formula I in which Z represents oxygen, may be prepared by reacting an alkaline isocyanate and preferably potassium isocyanate with a salt, and preferably with a monohalogenohydrate or a monoacetate, of a compound having the formula:

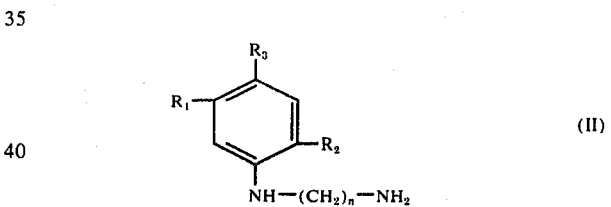

in which $R_1$, $R_2$ and $n$ have the significance hereinbefore indicated, $R_3$ represents an $NO_2$ or $NH_2$ group and, when $R_3$ represents an $NO_2$ group, the latter is transformed into an $NH_2$ group by catalytic hydrogenation, using hydrazine hydrate in the presence of Raney's nickel, or by one of the conventional methods of reducing a nitro group, for example by using sodium hydrosulfite in an alkaline medium or by catalytic hydrogenation, such as hydrogenation in an acetic medium in the presence of palladium on charcoal.

The method of preparation which utilizes as a starting material a compound according to formula (II) in which $R_3$ represents an $NO_2$ group, and in which said compound is reacted with an isocyanate, and the $NO_2$ group is then reduced by catalytic hydrogenation with hydrazine hydrate in the presence of Raney's nickel, constitutes a novel process.

The compounds according to formula (II) which are used as the starting material may be prepared by condensing an alkylene diamine having the formula $H_2N-(CH_2)_n-NH_2$, which may be in hydrate form, on a compound having the formula:

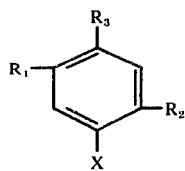

in which X represents a halogen, and preferably chlorine or bromine, and $R_1$, $R_2$ and $R_3$ have the significance above indicated.

The N-(ω-thioureidoalkyl) paraphenylenediamines of formula I in which Z represents a sulphur atom may be prepared by reacting in a first step carbon disulfide and sodium hydroxide with the above compound of formula II in which $R_3$ represents an $NO_2$ group. This yields the corresponding dithio carbamate, which is transformed in a second step by means of ethyl chloroformiate into isothiocyanate, which is then transformed into para-[N-(ω-thioureidoalkyl)]aminonitrobenzene by reaction with ammonia. The nitro group of this compound is then reduced in a conventional manner. Several examples of the preparation and use of the compounds according to the invention will now be described purely by way of illustration.

EXAMPLE 1

Preparation of N-(β-ureidoethyl) para-phenylenediamine from para-[N-(β-aminoethyl)]aminonitrobenzene.

1. Preparation of para-[N-(β-ureidoethyl)]amino nitrobenzene 37 g (0.2 mole) of para-[N-(β-amino-ethyl)]amino nitrobenzene is dissolved in 200 cm³ of water at 30° C, to which 15 cm³ (0.26 mole) of acetic acid had been added. 17 g (0.21 mole) of potassium isocyanate is then rapidly added. The desired product precipitates immediately in a form which is very difficult to dry. 150 cm³ of acetic acid is added to the reaction mixture and it is heated until the urein is completely dissolved. After slow cooling, drying yields 33 g of para-[N-(β-ureidoethyl)]amino nitrobenzene in a well crystallized form, which is practically prue and melts at 187° C.

2. Preparation of N-(β-ureidoethyl) para-phenylenediamine 94 g (0.42 mole) of para-[N-(β-ureidoethyl)]amino nitrobenzene is added little by little, while stirring, to 950 cm³ of a 3 N solution of NaOH containing 285 g of technical hydrosulfite, which has first been heated to 60° C. When the addition has been completed the reaction mixture is kept at 70° C until decoloration is complete. The mixture is then filtered, cooled and dried after salting out. The result is 46 g of N-(β-ureidoethyl) para-phenylenediamine which, after recrystallization in isopropyl alcohol, melts at 126°.

| Analysis | Calculated for $C_9H_{14}N_4O$ | Found |
| --- | --- | --- |
| C % | 55.67 | 55.59 |
| H % | 7.22 | 7.39 |
| N % | 28.86 | 28.86 |

EXAMPLE 2

Preparation of N-(β-ureidoethyl)para-phenylenediamine from N-(β-aminoethyl)para-phenylenediamine monohydrobromide.

2.43 g (0.03 mole) of potassium isocyanate is added to 4.6 g (0.02 mole) of N-(β-aminoethyl) para-phenylenediamine monohydrobromide in 20 cm³ of water. This mixture is heated for 5 minutes at 50° C under a nitrogen atmosphere. It is then cooled and salted out, using a concentrated solution of sodium hydroxyde. Drying then yields the crude product in a very impure form. After recrystallization in normal butyl alcohol 0.96 g of N-(β-ureidoethyl) para-phenylenediamine is obtained. This melts at 126°.

EXAMPLE 3

Preparation of 4-amino-2-methyl-N-(β-ureidoethyl) aniline.

This product is prepared in the following manner:

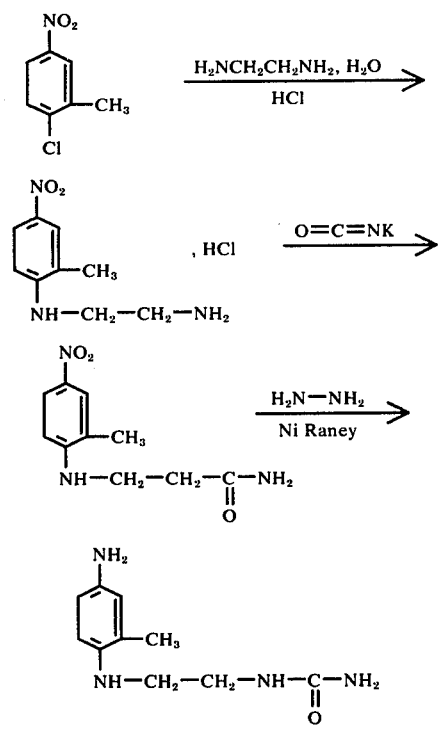

4-nitro-2-methyl-N-(β-aminoethyl) aniline monohydrochloride is obtained by reacting ethylene diamine with 2-chloro-5-nitro-toluene. This monohydrochloride is then reacted with potassium isocyanate to produce 4-nitro-2-methyl-N-(β-ureidoethyl) aniline, which is reduced with hydrazine and Raney's nickel to 4-amino-2-methyl-N-(β-ureidoethyl) aniline.

First Step — Preparation of 4-nitro-2-methyl-N-(β-aminoethyl) aniline monohydrochloride 51.45 g (0.3 mole) of 2-chloro-5-nitro-toluene is added to 200 cm³ (2.5 moles) ethylenediamine hydrate. The mixture is heated at reflux for 5 hours, and the excess of ethylene diamine is then eliminated under vacuum. The residue is treated with 300 cm³ of a 5N solution of hydrochloric acid, Drying yields 60.5 g of 4-nitro-2-methyl-N-(β-aminoethyl)aniline monohydrochloride, which is washed with acetone.

Second Step — Preparation of
4-nitro-2-methyl-N-(β-ureidoethyl) aniline 24.3 g (0.3 mole) of potassium isocyanate in solution in 75 cm³ of water is added to 57.9g (0.25 mole) of 4-nitro-2-methyl-N-(β-aminoethyl) aniline monohydrochloride in 235 cm³ of water at 60°. After keeping the reaction mixture for 15 minutes in a boiling water bath, drying yields 48 g of 4-nitro-2-methyl-N-(β-ureido-ethyl)aniline which, after recrystallization in acetic acid, melts at 186° C.

Third Step — Preparation of 4-amino-2-methyl N-(β-ureidoethyl)aniline 11.9 g (0.05 mole) of 4-nitro-2-methyl-N-(β-ureido-ethyl)aniline and 14 cm³ (0.28 mole) hydrazine hydrate are introduced into 160 cm³ of methanol. The mixture is brought to reflux and about 2 g of Raney's nickel is added. Heating is continued until the solution becomes decolorized. After eliminating the nickel by filtration, the methanol is evaporated under vacuum and 9 g of a crystallized residue is obtained which, after recrystallization in nitromethane, yields 8.2 g of 4-amino-2-methyl-N-(β-ureidoethyl)aniline, which melts at 143° C.

| Analysis | Calculated for $C_{10}H_{16}N_4O$ | Found |
|---|---|---|
| C % | 57.69 | 57.69 – 57.77 |
| H % | 7.69 | 7.69 – 7.72 |
| N % | 26.92 | 26.92 – 26.77 |

EXAMPLE 4

Preparation of 4-amino-2-methoxy-N-(β-ureidoethyl) aniline, utilizing the following reaction:

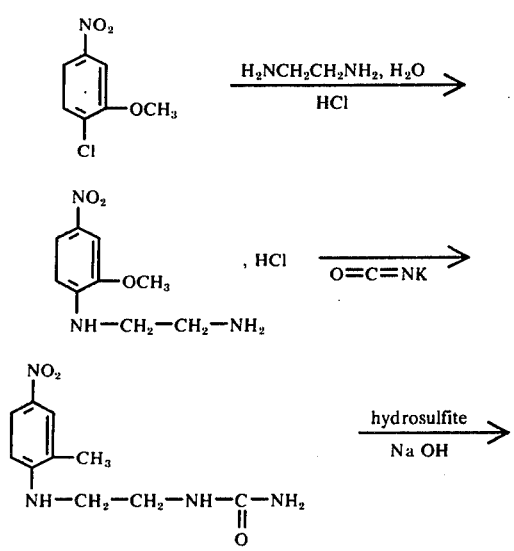

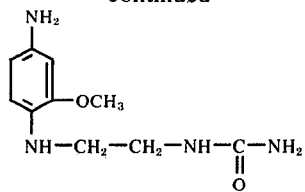

Ethylene diamine is reacted with 2-chloro-5-nitroanisole to form 4-nitro-2-methoxy-N-(β-aminoethyl)aniline which is isolated in the form of its monohydrochloride. This monohydrochloride is reacted with potassium isocyanate to form 4-nitro-2-methoxy-N-(β-ureidoethyl) aniline which is reduced by a sodium hydrosulfite solution to 4-amino-2-methoxy-N-(β-ureidoethyl) aniline.

First Step — Prepartion of
4-nitro-methoxy-N-(β-aminoethyl) aniline monohydrochloride 31 g (0.165 mole) of 2-chloro-5-nitro-anisole is added to 130 cm³ (1.65 mole) ethylenediamine hydrate. The reaction mixture is heated at reflux for five hours, and the excess of ethylenediamine driven off under vacuum. The residue is treated with 200 cm³ of a 5N hydrochloric acid solution, and dried, yielding 30 g of 4-nitro-2-methoxy-N(β-aminoethyl) aniline, which is washed with acetone.

Second Step — Preparation of
4-nitro-2-methoxy-N-(β-ureidoethyl)aniline 3.9 g (0.048 mole) of potassium isocyanate in solution in 12 cm³ of water is added to 9.4 g (0.038 mole) of 4-nitro-2-methoxy-2N-(β-ureidoethyl) aniline monohydrochloride in 40 cm³ of water at 50° C. After keeping the reaction mixture at 50° for 15 minutes drying yields 7g of 4-nitro-2-methoxy-N-(β-ureidoethyl) aniline which after recrystallization in aqueous acetic acid, melts at 183° C.

| Anaylsis | Calculated for $C_{10}H_{14}N_4O_4$ | Found |
|---|---|---|
| C % | 47.24 | 46.99 – 47.18 |
| H % | 5.51 | 5.72 – 5.62 |
| N % | 22.05 | 21.77 – 21.64 |

Third Step — Preparation of
4-amino-2-methoxy-N-(β-ureidoethyl) aniline 30 g (0.118 mole) of 4-nitro-2-methoxy-N-(β-ureidoethyl) aniline is introduced little by little, while stirring and cooling, sufficiently to avoid any increase in temperature into 300 cm³ of a 3N solution of sodium hydroxide to which 120 g of sodium hydrosulfite has been added and which has been brought to 70° C.

After decoloration of the reaction mixture, it is dried, washed first with water and then with alcohol. The yield is 18 g of 4-amino-2-methoxy-N-(β-ureidoethyl) aniline which, after recrystallization in nitromethane, melts at 164° C.

| Analysis | Calculated for $C_{10}H_{16}N_4O_2$ | Found |
|---|---|---|
| C % | 53.57 | 53.41 |

| Analysis | Calculated for $C_{10}H_{16}N_4O_2$ | Found |
|---|---|---|
| H % | 7.14 | 7.06 |
| N % | 25.00 | 25.03 |

EXAMPLE 5

Preparation of 4-amino-2-chloro-N-($\beta$-ureidoethyl) aniline, utilizing the following sequence of reactions

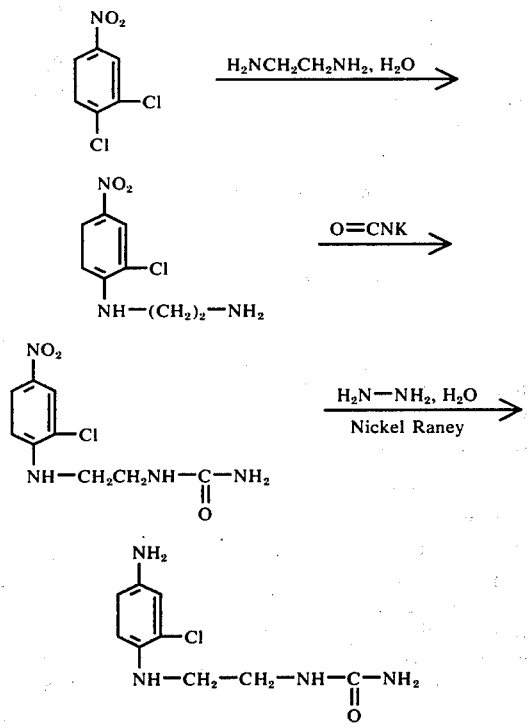

Ethylene diamine is reacted with 3,4-dichloronitrobenzene to form 4-nitro-2-chloro-N-($\beta$-aminoethyl) aniline, which is reacted in an acetic solution with potassium isocyanate to form 4-nitro-2-chloro-N-($\beta$-ureidoethyl) aniline. This latter compound is reduced with hydrazine in the presence of Raney's nickel, yielding 4-amino-2-chloro-N-($\beta$-ureidoethyl) aniline.

First Step — Preparation of 4-nitro-2-chloro-N-($\beta$-aminoethyl) aniline 192 g (1 mole) of 3,4-dichloro-nitrobenzene is added to 810 cm³ (10 moles) ethylene diamine hydrate. The reaction mixture is heated at reflux for 4 hours and then poured into 2.5 liters of ice water. Drying yields 205 g of 4-nitro-2-chloro-N-($\beta$-aminoethyl) aniline which, after recrystallization in absolute ethanol, melts at 116° C.

Second Step — Preparation of 4-nitro-2-chloro-N-($\beta$-ureidoethyl) aniline 100 g (0.46 mole) of 4-nitro-2-chloro-N-($\beta$-aminoethyl) aniline is dissolved in a liter of water to which 29 cm³ of acetic acid has been added. 41.3 g (0.51 mole) of potassium isocyanate is added to this reaction mixture, which is then left at the ambient temperature for 2 hours. Drying yields 110 g of 4-nitro-2-chloro-N-($\beta$-ureidoethyl) aniline which, after washing with dilute acetic acid and with water, followed by recrystallization in nitromethane, melts at 188° C.

| Analysis | Calculated for $C_9H_{11}O_3N_4Cl$ | Found |
|---|---|---|
| C % | 41.77 | 42.09 – 42.16 |
| H % | 4.25 | 4.32 – 4.33 |
| N % | 21.66 | 21.64 |
| Cl % | 13.73 | 13.33 – 13.39 |

Third Step — Preparation of 4-amino-2-chloro-N-($\beta$-ureidoethyl) aniline 51.7 g (0.2 mole) of urein and 50 cm³ (1 mole) of hydrazine hydrate is introduced into 600 cm³ of methanol. The mixture is brought to reflux and about 8 g of Raney's Nickel is added little by little. Reflux is continued until the solution is decolorized. After eliminating the nickel by filtration and concentrating half the mother liquor under vacuum, cooling and drying yields 32 g of 4-amino-2-chloro-N-($\beta$-ureidoethyl) aniline which, after recrystallization in methylisobutylketone, melts at 160° C.

| Analysis | Calculated for $C_9H_{13}ON_4Cl$ | Found |
|---|---|---|
| C % | 47.26 | 47.94 – 47.72 |
| H % | 5.69 | 5.79 – 5.75 |
| N % | 24.51 | 24.21 – 24.32 |
| Cl % | 15.53 | 15.15 |

EXAMPLE 6

The following solution is prepared:

| | |
|---|---|
| - N-($\beta$-ureidoethyl)para-phenylenediamine | 1 g |
| - meta-aminophenol | 3 g |
| - 20% lauryl ammonium sulfate, that is to say, aqueous ammonium laurylsufate solution, the concentration of which is 20% as referred to lauryl alcohol | 200 g |
| - ethylene diamine tetra-acetic acid | 3 g |
| - 20% ammonia | 100 g |
| - 40% sodium bisulfite aqueous solution | 10 g |
| - water, q.s.p. | 1000 g |

When this solution is mixed with an equal weight of 6% hydrogen peroxide and applied for 30 minutes to 100% white hair, an eggplant shade is produced.

EXAMPLE 7

The following solution is prepared:

| | |
|---|---|
| - 3-N-carbamylmethylamino-phenol | 2.5 g |
| - N-($\beta$-ureidoethyl)para-phenylenediamine | 1.5 g |
| - 20% lauryl ammonium sulfate | 200 g |
| - ethylene diamine tetra-acetic acid | 3 g |
| - 20% ammonia | 100 g |
| - 40% sodium bisulfite | 10 g |
| - Water, q.s.p. | 1000 g |

When this solution is mixed with an equal weight of 6% hydrogen peroxide and applied for 30 minutes to 100% white hair, a violet gray results.

EXAMPLE 8

The following solution is prepared:

| | |
|---|---|
| - N-(β-ureidoethyl)para-phenylenediamine | 1 g |
| - resorcinol | 3 g |
| - 20% lauryl ammonium sulfate | 200 g |
| - ethylene diamine tetra-acetic acid | 3 g |
| - 20% ammonia | 100 g |
| - 40% sodium bisulfite | 10 g |
| - water, q.s.p. | 1000 g |

This solution, when mixed with an equal weight of 6% hydrogen peroxide and applied for 30 minutes to 100% white hair, produces a bright golden chestnut.

EXAMPLE 9

The following solution is prepared:

| | |
|---|---|
| - N-(β-ureidoethyl)para-phenylenediamine | 1 g |
| - para-toluylenediamine | 1 g |
| - 2,4-diamino-anisole sulfate | 5 g |
| - 4-γ-aminopropylamino-2-methylamino-anthraquinone | 1 g |
| - 20% lauryl ammonium sulfate | 200 g |
| - ethylene diamine tetra-acetic acid | 3 g |
| - 20% ammonia | 100 g |
| - 40% sodium bisulfite | 10 g |
| - Water, q.s.p. | 1000 g |

This solution, when mixed with an equal weight of 6% hydrogen peroxide and applied for 30 minutes to 100% white hair, produces a bluish black.

EXAMPLE 10

The following solution is prepared:

| | |
|---|---|
| - N-(β-ureidoethyl) para-phenylenediamine | 1 g |
| - 3-hydroxy-phenylurea | 2 g |
| - 20% lauryl ammonium sulfate | 200 g |
| - ethylene diamine tetra-acetic acid | 3 g |
| - 20% ammonia | 100 g |
| - 40% sodium bisulfite | 10 g |
| - water, q.s.p. | 1000 g |

This solution, when mixed with an equal weight of 6% hydrogen peroxide and applied for 30 minutes to 100% white hair produces a grayish blue.

EXAMPLE 11

The following solution is prepared:

| | |
|---|---|
| - 4-Amino-2-methyl-N-(β-ureidoethyl) aniline | 1 g |
| - Meta amino phenol | 3.5 g |
| - 20% aqueous solution of lauryl ammonium sulfate | 200 g |
| - Ethylene diamine tetra-acetic acid | 3 g |
| - 20% Ammonia | 100 g |
| -40% Sodium bisulfite | 10 g |
| - Water, q.s.p. | 1000 g |

When this solution is mixed with an equal weight of 6% hydrogen peroxide, and applied to 100% white hair for 30 minutes, a deep gray shade results.

EXAMPLE 12

The following solution is prepared:

| | |
|---|---|
| - 4-Amino-2-methoxy-N-(β-ureidoethyl) aniline | 1 g |
| - 2,4-diamino anisole sulfate | 4 g |
| - 20% aqueous solution of lauryl ammonium sulfate | 200 g |
| - Ethylene diamino tetra-acetic acid | 3 g |
| - 20% Ammonia | 100 g |
| - 40% Sodium Bisulfite | 10 g |
| - Water q.s.p. | 1000 g |

This solution, when mixed with an equal weight of 6% hydrogen peroxide and applied for 30 minutes to 100% white hair, produces a greenish gray shade.

EXAMPLE 13

The following solution is prepared:

| | |
|---|---|
| - 4-Amino-2-chloro-N-(β-ureidoethyl) aniline | 1 g |
| - Meta amino phenol | 3.5 g |
| - 20% aqueous solution of lauryl ammonium sulfate | 200 g |
| - Ethylene diamino tetra-acetic acid | 3 g |
| - 20% Ammonia | 100 g |
| - 40% sodium bisulfite | 10 g |
| - water, q.s.p. | 1000 g |

This solution, when mixed with an equal weight of 6% hydrogen peroxide and applied to 30 minutes for 100% white hair produces a rose blonde shade.

The dye compounds of this invention may be placed in any suitable carrier such as water, alcohol etc., and they may be in any suitable form such as solution, gel, cream, aerosol, etc. Suitable carriers such as gelling agents, aerosol compositions, etc. are set forth in many text books, such as Cosmetic Materials, Vol. I and II by Harry.

Illustrative oxidation dyes of this invention are:

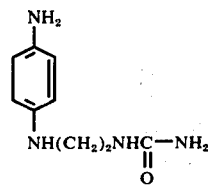

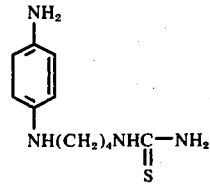

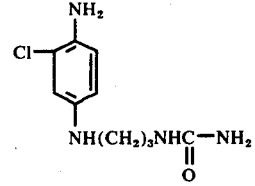

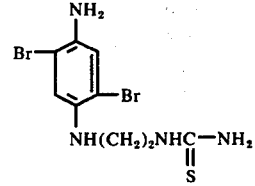

-continued

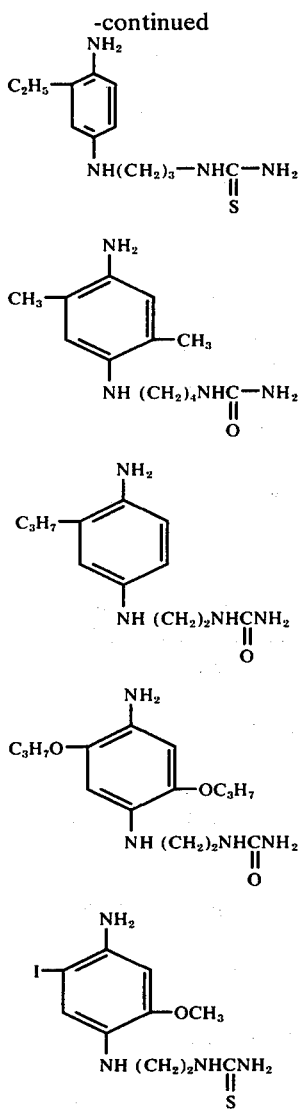

What is claimed is:

1. A compound for dyeing keratinic fibers and in particular human hair having the formula:

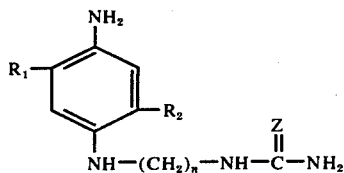

wherein $R_1$ and $R_2$ each independently are selected from the group consisting of hydrogen, halogen, alkyl having 1–3 carbon atoms and alkoxy having 1–3 carbon atoms, $n$ is a whole number ranging between 2 and 4 Z is selected from the group consisting of oxygen and sulfur.

2. The compound of claim 1 which is N-(β-ureidoethyl) paraphenylenediamine.

3. The compound of claim 1 wherein the alkyl group of $R_1$ or $R_2$ is methyl.

4. The compound of claim 1 wherein the alkoxy group of $R_1$ or $R_2$ is methoxy.

5. The compound of claim 1 wherein Z is oxygen.

6. The compound of claim 1 wherein Z is sulfur.

7. A method for preparing N-(β-ureido alkyl) paraphenylenediamine of the formula

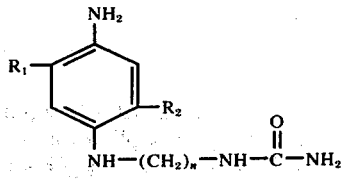

wherein $R_1$ and $R_2$ each independently are selected from the group consisting of hydrogen, halogen, alkyl having 1–3 carbon atoms and alkoxy having 1–3 carbon atoms and n is a whole number between 2–4 inclusive comprising (a) reacting alkaline isocyanate with a member selected from the group consisting of the monohalogenohydrate and monoacetate of a compound of the formula

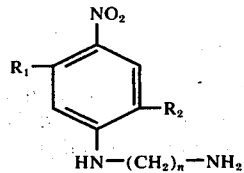

wherein $R_1$, $R_2$ and n have the meaning given above in an aqueous medium to produce a compound of the formula

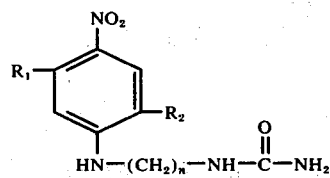

wherein $R_1$ and $R_2$ have the meaning given above, (b) recovering the compound from step (a), (c) adding to the compound recovered from (b) methanol and as a reducing agent, hydrazine hydrate, and a Raney nickel catalyst, (d) heating the resulting mixture until said mixture becomes colorless whereby the nitro substituent of said compound is reduced to amino and (e) recovering said N-(β-ureidoalkyl) paraphenylenediamine.

8. The method of claim 7 wherein said isocyanate is potassium isocyanate.

9. A method for preparing a N-(β-ureidoalkyl) paraphenylenediamine of the formula

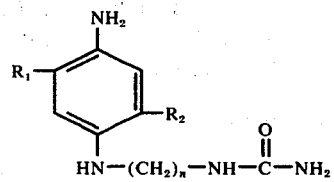

wherein $R_1$ and $R_2$ each independently are selected from the group consisting of hydrogen, halogen, alkyl having 1–3 carbon atoms and alkoxy having 1–3 carbon atoms and n is a whole number between 2-4 inclusive comprising a. reacting alkaline isocyanate with a compound of the formula

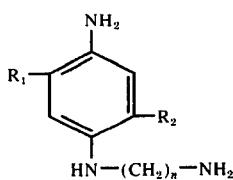

in an aqueous medium at a temperature of 50° C for 5 minutes and b. recovering said N-(β-ureidoalkyl) para-phenylenediamine.

10. The method of claim 9 wherein said isocyanate is potassium isocyanate.

11. A method for preparing N-(β-ureidoalkyl) para-phenylenediamine of the formula

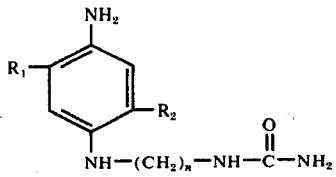

wherein $R_1$ and $R_2$ each independently are selected from the group consisting of hydrogen, halogen, alkyl having 1-3 carbon atoms and alkoxy having 1-3 carbon atoms and n is a whole number between 2-4 inclusive, comprising a. reacting alkaline isocyanate with a member selected from the group consisting of the monohalogenohydrate and monoacetate of a compound of the formula

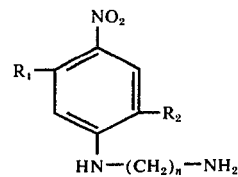

wherein $R_1$, $R_2$ and n have the meaning given above in an aqueous medium at a temperature ranging from ambient to 60° C to produce a compound of the formula

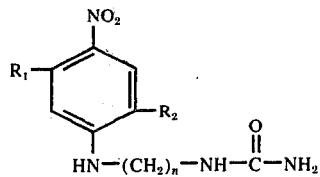

wherein $R_1$ and $R_2$ have the meaning given above, b. adding to the compound resulting from (a) as a reducing agent, sodium hydrosulfite, in an aqueous alkaline medium, c. heating the resulting mixture to a temperature of about 70° C for a time sufficient to reduce the nitro substituent of said compound to amino and d. recovering said N-(β-ureidoalkyl) para-phenylenediamine.

12. The method of claim 11 wherein said isocyanate is potassium isocyanate.

* * * * *